United States Patent
Schulz et al.

(10) Patent No.: US 10,391,278 B2
(45) Date of Patent: Aug. 27, 2019

(54) PUSH DEVICE FOR THE AXIAL INSERTION OF AN ELONGATE, FLEXIBLE BODY

(75) Inventors: Heike Schulz, Berlin (DE); Daniel Roehn, Berlin (DE)

(73) Assignee: ECP ENTWICKLUNGSGESELLSCHAFT MBH, BerlinAmtsgericht Berlin (Charlottenburg) (DE)

( * ) Notice: Subject to any disclaimer, the term of this patent is extended or adjusted under 35 U.S.C. 154(b) by 830 days.

(21) Appl. No.: 13/261,735

(22) PCT Filed: Mar. 6, 2012

(86) PCT No.: PCT/EP2012/001062
§ 371 (c)(1),
(2), (4) Date: Oct. 15, 2013

(87) PCT Pub. No.: WO2012/119782
PCT Pub. Date: Sep. 13, 2012

(65) Prior Publication Data
US 2014/0039465 A1 Feb. 6, 2014

Related U.S. Application Data

(60) Provisional application No. 61/451,222, filed on Mar. 10, 2011.

(30) Foreign Application Priority Data

Mar. 10, 2011 (EP) .................................... 11075043

(51) Int. Cl.
*A61M 25/01* (2006.01)

(52) U.S. Cl.
CPC .............................. *A61M 25/0113* (2013.01)

(58) Field of Classification Search
CPC .... A61M 25/01; A61M 25/0113; A61M 1/12; A61M 25/00; A61M 25/0105; A61M 25/0116
USPC ............................................. 604/528; 600/16
See application file for complete search history.

(56) References Cited

U.S. PATENT DOCUMENTS

| | | |
|---|---|---|
| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |

(Continued)

FOREIGN PATENT DOCUMENTS

| | | |
|---|---|---|
| AT | 006 847 U2 | 5/2004 |
| CA | 1008330 A1 | 4/1977 |

(Continued)

*Primary Examiner* — Imani N Hayman
*Assistant Examiner* — Tiffany Legette
(74) *Attorney, Agent, or Firm* — White & Case LLP (57) ABSTRACT

With a push device for the axial insertion of an elongate, flexible body, in particular of a flexible tube, a cable or similar elements into a sheath, and axial force introduction unit is provided, which by way of a non-positive fit or a positive fit, applies a push movement onto the elongate body and is arranged in a stationary manner relative to the sheath or is guided on a predefined movement path.

18 Claims, 8 Drawing Sheets

(56) References Cited

U.S. PATENT DOCUMENTS

| | | |
|---|---|---|
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,389,100 A * | 2/1995 | Bacich .............. A61M 25/0119 604/159 |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monett et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,358,199 B1 * | 3/2002 | Pauker .............. A61M 25/0113 600/102 |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Scmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser |
| 6,726,675 B1 * | 4/2004 | Beyar .............. A61M 25/0105 600/106 |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,927,068 B2 | 4/2011 | McBride et al. |
| 7,934,909 B2 | 5/2011 | Neusser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0114339 A1 * | 5/2008 | McBride .............. F04D 3/00 604/891.1 |
| 2008/0132747 A1 | 6/2008 | Shifflette |
| 2008/0262584 A1 | 10/2008 | Bottomley et al. |
| 2008/0300592 A1 | 12/2008 | Weitzner et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0076308 A1 * | 3/2010 | Wenderow .......... A61M 25/0113 600/434 |
| 2010/0268017 A1 | 10/2010 | Siess |
| 2011/0046553 A1 * | 2/2011 | Nagano ............ A61B 17/12113 604/156 |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2311977 A1 | 12/2000 |
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |

(56) References Cited

FOREIGN PATENT DOCUMENTS

| | | |
|---|---|---|
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 10 2006 054 250 A1 | 5/2008 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | WO 99/45994 A1 | 9/1999 |
| WO | 0027446 A1 | 5/2000 |
| WO | 0043054 A2 | 7/2000 |
| WO | 0062842 | 10/2000 |
| WO | 2001007760 A1 | 2/2001 |
| WO | 2001007787 A1 | 2/2001 |
| WO | 2001083016 A2 | 11/2001 |
| WO | WO 02/43791 A1 | 6/2002 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | WO 2009137410 A1 * | 11/2009 ......... A61M 25/0113 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

\* cited by examiner

PUSH DEVICE FOR THE AXIAL INSERTION OF AN ELONGATE, FLEXIBLE BODY

CROSS-REFERENCE TO RELATED APPLICATIONS

This application is a United States National Stage filing under 35 U.S.C. § 371 of International Application No. PCT/EP2012/001062, filed Mar. 6, 2012, which claims the benefit of U.S. Provisional Patent Application No. 61/451,222, filed on Mar. 10, 2011, and European Patent Application No. 11075043.7, filed Mar. 10, 2011, the contents of all of which are incorporated by reference herein in their entirety. International Application No. PCT/EP2012/001062 was published under PCT Article 21(2) in English.

BACKGROUND OF THE INVENTION

The invention lies in the field of mechanics, in particular of mechanical engineering and precision technology. It concerns those mechanical problems which arise on inserting a flexible, elongate body into an opening or sheath, due to its tendency to buckle. To buckle in the context of the present invention is also to be understood as to abruptly bend, and could also be described as kinking in a two-dimensional manner, in accordance with the German word "knicken".

Such flexible, elongate bodies may for example be cables, wires, threads, flexible tubings or a combination of such elements, which are typically to be inserted into sheaths or openings, tubes, hoses or generally cavities. Such an elongate body may also be a second sheath which is inserted into a first sheath or is to be held in a stationary manner with respect to this. If a resistance against a further pushing movement results when pushing such bodies, then the body must be prevented from buckling, in order to permit a further push movement, or corresponding radial deflection movements must be limited.

As a whole, amongst other things, it is case of designing the handling such that it is secure as possible. Thereby, it is advantageous if on introduction, a certain buckling angle is not exceeded and a certain bending radius is not fallen short of.

One application of the invention for example results on introducing a mechanical pipe cleaning device into a pipe conduit system, wherein the cleaning device is inserted with a flexible shaft.

Typically, such problems also result in medical technology, if for example a canulla or a catheter is to be inserted into a body opening, a lumen of the body or an artificial lumen Typical such situations are for example evident from the international patent application WO 02/43791 A1. There, it is described that an intravascular pump is introduced into a sheath, in order finally to be inserted it into a blood vessel of a human body. A further push movement takes place, also after the pump has passed the actual sheath region.

Since such pumps are to be pushed through a blood vessel over lengths of a few tens of centimeters within the body, one must reckon with a certain push resistance which renders necessary a certain push force on inserting. In particular with self-openable or self-expandable pumps heads, one is to reckon with an increased push resistance on account of the occurring restoring forces of the folded or compressed pump head. This is particularly due to the fact that because with such pumps, a flexible shaft which is envisaged for high rotation speeds and a long service life and which is sensitive to buckling runs within a catheter to be pushed, it must be ensured that the necessary push force may be applied onto the catheter without this buckling out or deflecting in another manner.

BRIEF SUMMARY OF THE INVENTION

It is therefore the object of the present invention, to provide a push device for the axial insertion of an elongate, flexible body into a sheath or for the secure mounting of such a body with respect to a sheath, which is constructed in an as simple as possible manner and which permits the simple production of a push movement and reliably prevents a deflection of the elongate body.

According to the invention, this object is achieved with the features specified in patent claim 1.

A holding unit is provided for this, which may be designed as an axial force introduction unit which by way of a non-positive or positive fit, exerts an axial holding force or push force onto the elongate body and which is arranged in a stationary manner relative to the sheath or is led on a defined movement path. Axial direction in this context is to be understood as the longitudinal axis direction of the sheath and/or the elongate body.

Since one may not often engage directly on an end of the elongate body, an axial force introduction unit must engage on the elongate body either by way of clamping, i.e. non-positive fit and corresponding static friction forces, or by way of a positive fit on the elongate body, inasmuch as this comprises suitable shape elements on the outer side. A corresponding clamping or a positive fit then permits the application of an axial force and thus a holding force and a push movement. For example, one may envisage the (first) sheath as well as the elongate body which indeed may also be formed as a (then second) sheath, each comprising a flange as a fit piece, wherein each of the flanges may be each inserted into a recess of the push device, or both flanges together maybe inserted into a single recess of the push device, in particular of the holding unit or of a guide device for the holding unit which may then be fastened on the sheath, said insertion being such that the flanges are fixed in the axial direction and/or radial direction.

Advantageously, the fit piece of the sheath is not displaceable in the push device, disregarding the necessary mechanical play.

The fit piece of the sheath may advantageously be rotatable about the insert direction of the push device in different positions, in particular with a cylinder-symmetrical design may also be inserted into the recess at any angular position.

After inserting the fit piece into the recess, this fit piece may either still be freely rotatably about the insert direction or also be non-positively fixed or positively fixed with respect to the rotation angle.

The push device may be able to be dismantled for inserting the flange or flanges into the recess or recesses and for example be designed as a longitudinally divided hollow body, in particular hollow cylinder. The recess may also comprise a rinsing device, so that a rinsing fluid for cleaning the fit piece/pieces may be introduced there from the outside through a channel.

Due to the fact that the holding unit/axial force introduction unit is arranged in a stationary manner to the (first) sheath, in the push device, the distance and the alignment of the unit may be selected such that the axial loading of the elongate body is well controllable and is easy to limit, that only safe radial forces and radial deflections are applied onto the elongate body and that the free length of the elongate body between the axial force introduction unit and the sheath may be defined or limited.

Even if the axial force introduction unit is led on a defined movement path, this path may be accordingly selected such that the tendency of the elongate body to break out laterally given a push movement is minimised. Moreover, a mechanical guide for the elongate body may be well dimensioned and positioned with a given movement path of the axial force introduction unit.

The guide of the axial force introduction unit may for example be realised by way of a single-stage or multi-stage telescopic guide, for example with concentric tubes, or by way of guiding in a rail or in a cylindrical cavity.

Advantageously, one may envisage the push device being mechanically coupled onto the sheath in a direct manner. This for example may be achieved by way of a central thread, a bayonet closure, by the application of adhesion forces, by way of a magnetic coupling, by way of an eccentric screw connection (for example by way of screws distributed on the periphery), by way of gluing, by way of electrostatic attraction forces, by way of elastic holding elements such as springs, clips or rubber cords or by way of insertion of a fit piece of the sheath into a fittingly shaped recess of the holding unit.

In particular, a deflection of the elongate body on entry into the sheath should be avoided, since a mechanical guiding and radial support is usually given or may be simply created in the sheath or in the flexible tube belonging to the sheath, and the risk of buckling plays less of a role behind the sheath or the flexible tube belonging to the sheath, on account of the reduced restoring forces.

By way of coupling the push device onto the sheath, the distance between the holding unit/axial force introduction unit and the sheath is limited, and a defined guiding of the elongate body and/or a radial supporting is made possible. Also it is particularly simple to fix the movement path of the axial force introduction unit, in the case that such is provided, with respect to the sheath.

For coupling, the sheath may for example comprise a flange or a plane front plate with an opening, into which the elongate body is to be introduced, wherein a corresponding counter-flange of the push device may be coupled onto the front plate or the flange. Thereby, usually releasable connection techniques may be applied or also the usual joining techniques such as gluing or other adhesive measures, which advantageously however are to create a releasable connection.

If by way of the push device, only the first sheath and an elongate body, for example a second sheath, are to be axially pressed against one another, then a flange or a front plate of the first sheath on the one hand and a flange of the second sheath or of another elongate body may be fixed to one another. However, for example a connection may also be created by way of insertion into one another, which is held by a non-positive or positive fit. What is important here, is that the forces for holding the connection are greater than the forces which are necessary for pushing the elongate body, so that the connection is not unintentionally released on pushing the elongate body.

A mechanical coupling may advantageously also be provided directly between the axial force introduction unit and the sheath. A radial guiding between the axial force introduction unit and the sheath may be minimised or completely left out by way of this. The constructional size of the push device may thus also be kept very low.

Advantageously, the push device may comprise a guide device which may be fastened on the sheath by way of a coupling and which radially supports the elongate body, wherein the axial force introduction unit is arranged either in a stationary manner relative to the guide device or is guided on a defined movement path. In this case, the guide device is provided between the axial force introduction unit and the sheath and either serves for bridging a distance between the axial force introduction device and the sheath, and with this rendering the application of a push force manageable, and/or with a given small distance between the axial force introduction unit and the sheath, to design this distance by way of the guide device, in a manner such that the elongate body may in no case radially deflect with this distance.

The axial force introduction unit may advantageously comprise a radial clamping device which by way of pressing a clamping tool onto the elongate body in the radial direction produces a bond which serves for applying a push force or holding force in the axial direction. The clamping tool may be designed in a movable manner for example and roll on the elongate body.

In particular, at least one, on particular two, three or four friction wheels may be provided as a clamping tool, which lie radially opposite one another at least partly with respect to the elongate body. The elongate body may then be clamped between the friction wheels and be radially supported by these. A push movement may be applied onto the elongate body by way of a drive of the friction wheels. One may also arrange several sets of friction wheels or knurled wheels one after the other in the longitudinal direction of the elongate body.

One may also envisage the friction wheels or at least one of them comprising a free-wheel means which permits a rotation in each case in only one direction, so that for example the friction wheels block and push the elongate body upon advancing the push device, and rotate the friction wheels in a manner such that the push device may be displaced with respect to the elongate body without force, upon retracting the push device. With this, the elongate body may for example be pushed in steps, for example by hand or by way of another drive, by way of displacement of the push device.

Such drives may for example be provided by way of electric motors on the friction wheels, so that the push device may stand still in a stationary manner. A reduced space requirement results with the application of the push device by way of this.

Generally, it may a make sense for the friction wheels to be able to be controlled with regard to their rotation, i.e. either be actively drivable or for example lockable in a controlled manner from the outside. The continuous drive of the push device by way of a rotation drive of the friction wheels for example also permits the control of the introduced push force in dependence on the advance, the advance speed or a detected counter-force. With this, one may prevent a catheter for example, which is inserted into a body, from being simply pushed further in the case that an increased resistance arises due to hitting a vessel wall. A suitable control may stop the advance procedure or slow it down. A suitable control which may designed in an electronic manner, may either control the advance force or the advance speed either according to a defined curve/characteristics or in dependence on the push resistance.

One may also advantageously envisage the clamping tool being provided with clamping jaws radially on both sides of the elongate body, and the clamping jaws with the elongate body fixed between them being movable in a guided manner with respect to the sheath and/or a guide device, essentially in the axial direction the elongate body.

The clamping jaws may thereby be designed as two or more bodies which are movable relative to one another in the radial direction with respect to the elongate body, and which for example may also be designed in a compliant manner, in particular softer that the elongate body itself. For this purpose, the clamping jaws should consist of a soft material such as plastic or elastomer for example or a coated with such a material. One may also envisage only a few of the clamping jaws being designed in a movable manner, whilst the other clamping jaws are fixed in a stationary manner.

For example, two, three, four, five or more clamping jaws may be provided, which lie opposite one another on the periphery of the elongate body.

Particularly advantageously, the clamping jaws may be formed by two or more parts for example of a hollow cylinder or of any other shape corresponding to the elongate body, said shape receiving the elongate body. The clamping jaws may then form sector bodies of the hollow cylinder. A hollow cylinder in this context is to be understood as a body which has an in particular cylindrical, continuous opening. Such a body may for example also have a cylindrical shape on its outer side. Instead of a hollow cylinder, one may also apply a different type of body with a continuous opening.

The respective sector bodies may for example have the same length as the hollow cylinder and be distributed on the periphery of the elongate body. The push device may also be designed in a manner such that first clamping jaws are arranged in a non-movable manner in the axial direction and consist of a material which has a low friction compared to the material of the elongate body. Second clamping jaws in contrast are axially movable and have a greater friction coefficient compared to the material of the elongate body, so that the elongate body may be pushed by the second clamping jaws against the first clamping jaws and may be slidingly moved in the axial direction on these, as on a guide rail. In this manner, the radial guiding for the elongate body may be realised by the clamping jaws, as well as the advance in the axial direction by way of individual ones of the clamping jaws.

The holding device may comprise a clamping device for the elongate body, said clamping device able to be clamped by hand by way of radial pressure and releasing the elongate body with the absence of an external pressure force. Spring elements may serve for this, which automatically opens the holding device/clamping device.

A method for realising the invention envisages the speed of the advance of the elongate body being controlled by a control device. Thereby the speed may be activated as a constant speed or also according to defined speed characteristics/time characteristics or speed characteristics/displacement characteristics.

If unforeseen resistances to the elongate body result with the advance movement, for example if this is inserted into a blood vessel of a patient, then the respective drive force may be increased by way of the control, in order to ensure the advance speed according to the defined characteristics.

However, one may also envisage a control which keeps the advance resistance or the advance force constant, so that the drive force onto the push device is reduced with the occurrence of increased push resistances on the elongate body, for example in order to prevent a buckling of the elongate body due to the increase of push forces, or with a medical application, for example if the elongate body is a catheter which is introduced into a body opening, to prevent an injury of the patient. In this case, the advance may also be completely stopped by way of the control, and the elongate body retracted a little. The increase of the push resistance may be signalled by a light on the outside on the push device as well as by way of an acoustic signal transducer.

Inasmuch as this is concerned, the push resistance may be measured and the push movement may be controlled with or without a closed loop in dependence on the push resistance. For this, a drive, for example an electric or pneumatic drive, and a suitable sensor, for example a current sensor for measuring the magnitude of the applied current strength, a voltage sensor or a suitable pressure sensor with the use of pneumatics, as well as a control device and correspond signal transducers are to be provided for this.

BRIEF DESCRIPTION OF THE DRAWINGS

The invention is hereinafter shown by way of one embodiment example and described hereinafter. Thereby are shown in:

FIG. 2 a pump device with a heart catheter pump and with a drive shaft which runs in a hose-like casing, FIG. 3 a push device in a three-dimensional view, FIG. 4 the push device of FIG. 3 in a lined representation, FIG. 5 a longitudinal section through the device of FIG. 4, FIG. 6 a guide device designed as a hand grip, in a longitudinal section with the front end of a sheath, FIG. 7 a guide device without an inserted sheath, FIG. 8 the guide device of FIG. 7 in a front view, FIG. 9 a push device with at least two friction wheels, FIG. 10 a plan view of the device according to FIG. 9, along the line indicated in FIG. 3 at IV-IV, FIG. 11 a similar view to that in FIG. 10, with four friction wheels distributed around the elongate body, FIG. 12 a similar view as in FIG. 11, additionally with electromechanical drives of the friction wheels, FIG. 13 an arrangement with two friction wheels which have friction surfaces which are concave in cross section, FIG. 14 a push device similar to that of FIG. 9, with which the friction wheels only serve for the radial support and a different type of axial force introduction is envisaged, FIG. 15 a view of the device of FIG. 14 along the line which is characterised there at IX-IX, FIG. 16 a further variant of the axial force introduction unit, FIG. 17 a cross section of the axial force introduction unit of FIG. 16, FIG. 18 a further design of the axial force introduction unit, FIG. 19 a cross sectional view along the line XIII-XIII of FIG. 18, FIG. 20 another variant of the axial force introduction unit of FIG. 18, FIG. 21 in a longitudinal section, a push device with axially stationary and axially movable clamping jaws, FIG. 22 a cross section of the device of FIG. 21 along the line characterised there at XVI-XVI and FIG. 23 a detail of the drive device for a push device.

DETAILED DESCRIPTION OF THE INVENTION

Figure 1:
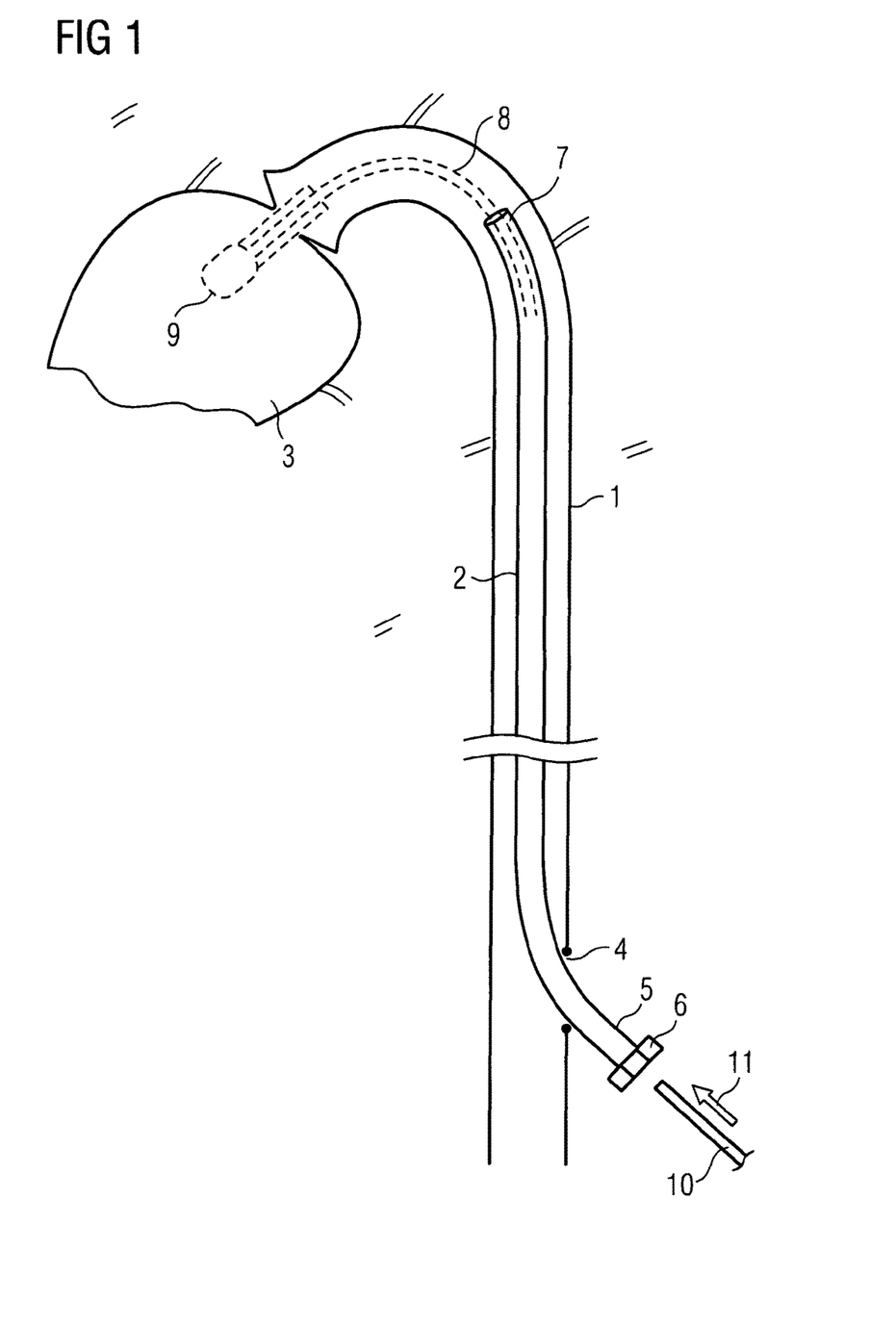
FIG. 1 the application of a heart catheter pump with a human heart.

FIG. 1 in a longitudinal section shows a blood vessel 1 with a first sheath 2 in the form of a flexible tubing or hose and which with its distal end projects into the blood vessel 1 in the direction of a heart chamber 3 up to the aortic arch.

The sheath 2 is introduced through an opening 4 into the blood vessel 1 and is ideally sealed there. The first sheath 2 at its proximal (outside the body) end 5 comprises a flange 6.

A heart catheter 8 which is designed in a hollow manner and in which a drive shaft for a heart pump 9 which is represented in a dashed manner, is shown at the distal end 7 of the sheath 2, also in a dashed manner. The pump 9 is inserted into the heart chamber 3 and comprises a rotor which rotates with a high rotation speed, driven by the shaft, in order to deliver blood out of the heart chamber into the blood vessel 1.

An elongate body 10 is represented at the proximal end 5 of the sheath 2, in front of the flange 6, and is to be introduced into the sheath 2 in the direction of the arrow 11. The elongate body 10 is shown only in sections there. In the shown case, the elongate body is formed for example by way of the heart catheter 8 which together with the flexible drive shaft arranged therein represents a flexible elongate body which is to be pushed through the sheath 2 into the blood vessel 1 and further into the heart chamber 3. Depending on the point, at which the heart catheter is inserted into a blood vessel (typically at a femoral artery), the advance displacement for the catheter is more than 80 cm in the patient body.

The elongate body 10 may consist of a heart catheter 8 which is surrounded by a second, flexible-tube-like sheath. This second sheath is then designed such that it keeps the radially compressible pump compressed. The second sheath may usefully already be premanufactured with the heart catheter 8 and the pump before use on a patient body.

The second sheath may then be axially held onto the first sheath and fixed there, for example by way of the push device according to the invention. Whilst the second sheath is pressed axially against the first sheath, the heart catheter may then be pushed through the second sheath into the first sheath and by way of this may be pushed into the blood vessel.

A push device according to the invention may likewise be applied with the axial insertion of the heart catheter into the second sheath. This push device is then applied onto the second sheath opposite to the first sheath and encloses the section of the heart catheter in front of the second sheath.

Figure 2:
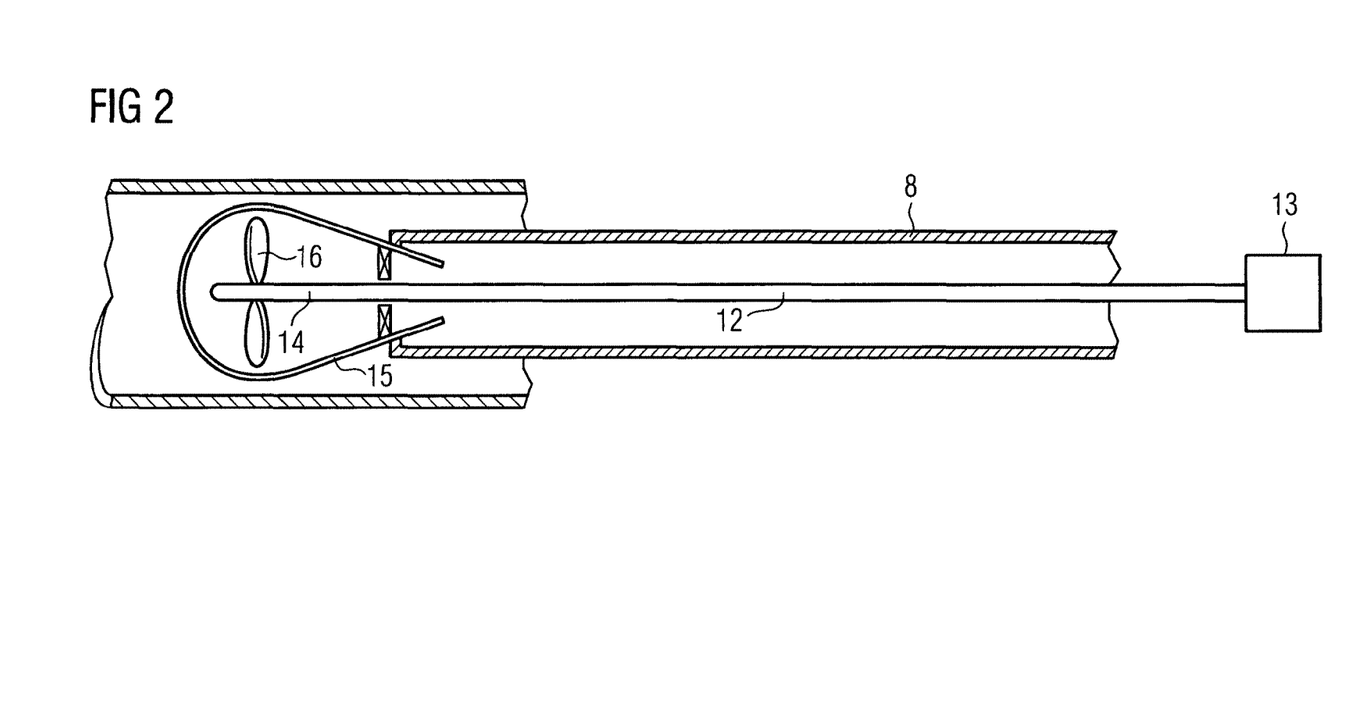

FIG. 2 shows a more detailed, but schematic representation of the pump catheter 8 with the flexible drive shaft 12. This is connected proximally to a drive in the form of a motor 13 and distally to a drive hub 14 within a pump housing 15. The hub 14 carries rotor blades 16 for delivery of a fluid or blood.

Figure 3:
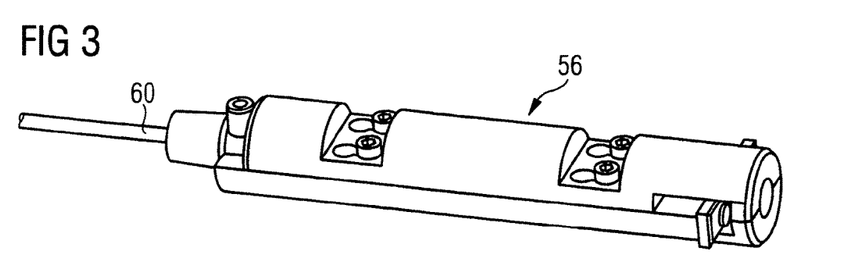

FIG. 3 shows one design of a push device in a three-dimensional view.

Figure 4:
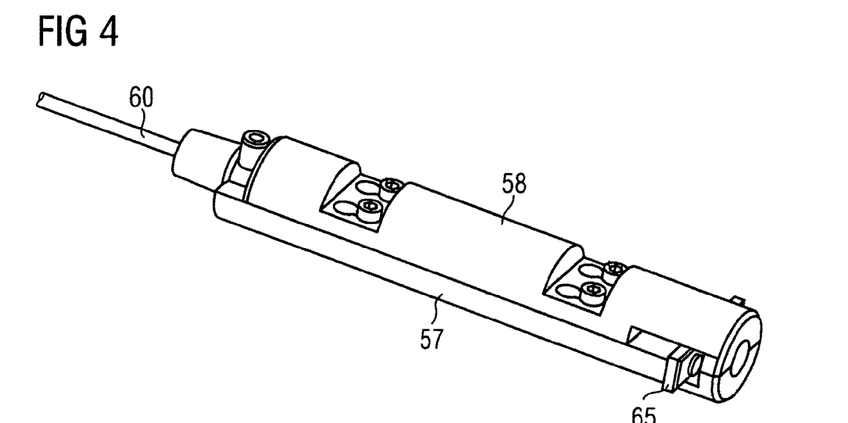
Figure 5:
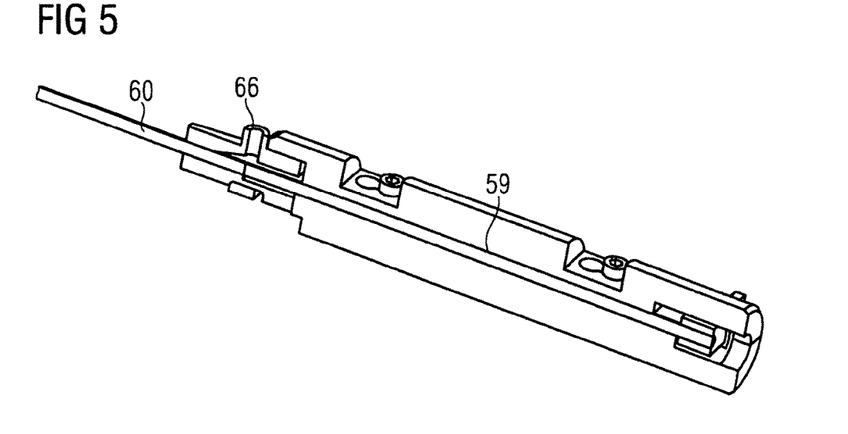

FIG. 4 shows the same view as an outline drawing and FIG. 5 a longitudinal section.

Figure 6:
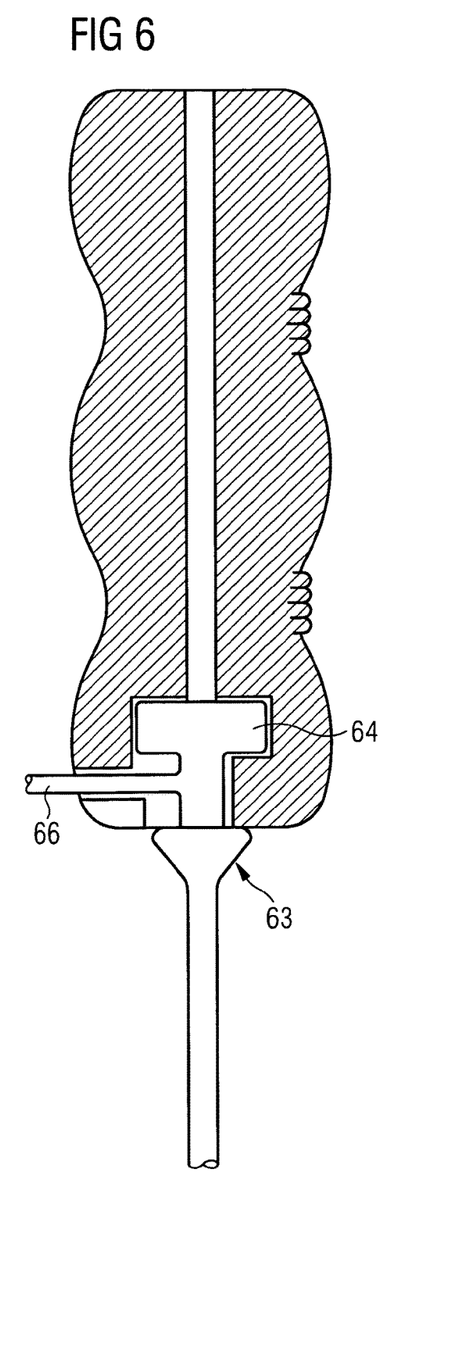
Figure 7:
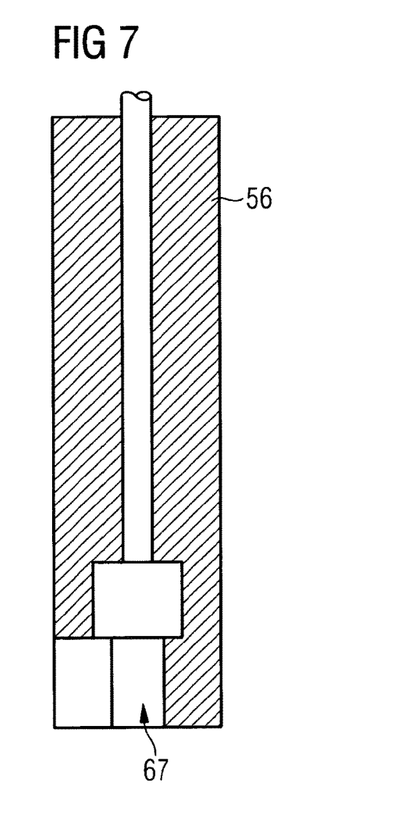

A guide device 56 in the form of a hollow cylinder divided into two, with a lower half 57 and with an upper half 58 is shown. The cylindrical cavity 59 receives the elongate body 60 to be pushed, as well as a second sheath and supports it in a radial manner. The upper half 58 is connected to the lower half 57 via screws 61, 62 which slide in elongate holes. The elongate holes are widened at one end, so that the upper half may be removed after displacing this. By way of this, the elongate body with the second sheath, just as the first sheath, may be inserted with its flange 64 without any problem, and the front-side end 63 of the sheath (cf. FIG. 6) in particular the flange 64 may be inserted into the undercut cavity 67 of the hollow cylinder 56 (FIGS. 6, 7). A reliable, releasable coupling of the guide device onto the sheath is ensured by way of this. A channel of a rinsing device which runs out into the cavity 67 is indicated in FIG. 5 with the reference numeral 66.

A holding unit/axial force introduction device may comprise recesses for tear tabs 65 of a second sheath, if the second sheath is designed as a so-called "peel-off" sheath. This means that the second sheath on account of its material structure (molecular alignment, anisotropic structure) and/or the incorporation of predefined breakage locations (perforation), is set up to be longitudinally torn open and removed, after pushing through a heart catheter.

Figure 8:
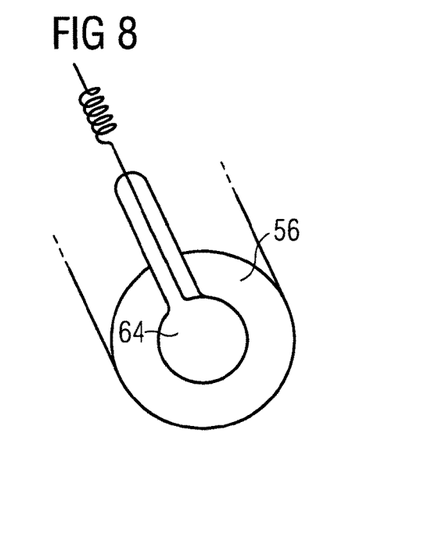

FIG. 8 shows a further illustration of a cross section of FIG. 6.

Figure 9:
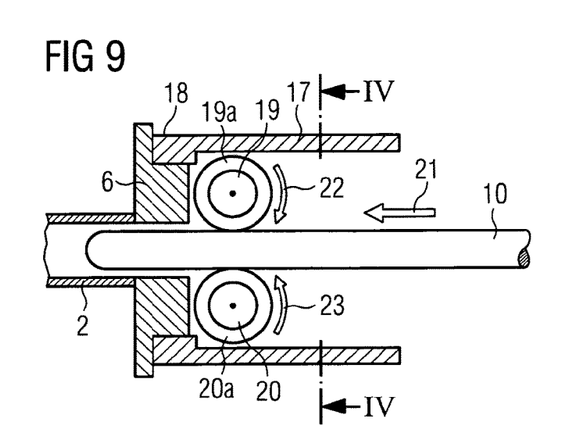

FIG. 9 specifically shows another embodiment of an advance device, wherein the flange 6 of the first sheath 2 is shown on the left side and the push device in the right region of the figure. The push device comprises a tubular housing 17 whose distal end 18 may be pushed onto the flange 6 and is fixed there with respect to the flange 6. The fixation may for example be realised by way of a central thread on the flange 6 as well as on the housing end 18 or by way of a bayonet connection between these parts. Other types of screw connections or and other bonding connections such as gluing or magnetic bonding are conceivable. It makes sense if the connection between the push device and the flange 6 of the sheath can be easily released again. The push device may also comprise a cavity for receiving and fixing the flange 6, as well as an opening for incorporating the flange into the cavity, At least two friction wheels 19, 20 as part of an axial force introduction device or holding unit are rotatably mounted within the housing 17 and on their periphery each have a friction coating 19a, 20a which has a greater coefficient of friction compared to the material of the elongate body 10. The elongate body 10 is typically clamped in between the friction wheels 19, 20. The elongate body may thereby be a catheter as well as a second sheath.

The friction wheels 19, 20 may for example be controllable with regard to the rotation ability. If they are blocked, as a whole the elongate body may be advanced in the direction of the arrow 21 by way of axial movement of the push device together with the friction wheels if these are movable in a guided manner in the housing 17. If the push device is retracted opposite to the direction of the arrow 21, then the friction wheels 19, 20 may be released for example by way of a control or a freewheel, so that with this movement of the push device, the elongate body 10 is not caught, but remains in the position relative to the sheath 2. The friction wheels 19, 20 may be blocked again before a renewed advance of the push device in the direction of the arrow 21. For example, for realising such a drive mechanism, the housing 17 may be axially advancable and retractable on a connection of the flange 6.

Another variant of the drive may envisage the friction wheels 19, 20 being able to be driven in the direction of the arrows 19, 20 when the push device is stationary, in order to push the elongate body 10 in the direction of the arrow 21. This variant has the advantage that the speed of the friction wheels 19, 20 or the torque may be detected for example by way of the current of an electric motor driving the friction wheels. The respectively detected variables may be used for controlling the advance speed of the elongate body or for the control of the push force, in order to limit this and thus to prevent injuries on inserting a catheter into a lumen within a body of a patient. Alternatively, the push force may also be limited by way of a slip coupling for example.

Figure 10:
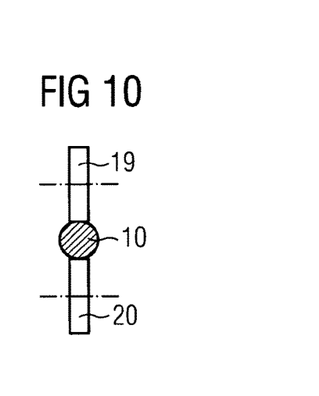

FIG. 10 in a plan view along the line IV-IV according to FIG. 3 shows the two friction wheels 19, 20 as well as the elongate body 10 which is clamped between them.

Figure 11:
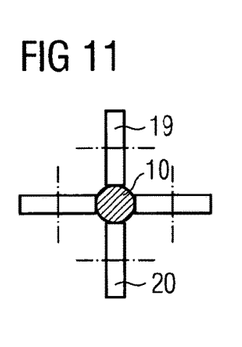

In FIG. 11 it is shown that indeed also more than two, for example four friction wheels 19, 20 may be provided distributed on the periphery of the elongate body. This may be three, five or six friction wheels for example.

A rotatable mounting is represented schematically for each individual friction wheel by way of a stylised pivot. The friction wheels may be driveable for example by way of individual motoric drives or together via a coupling gear. One may also envisage only individual ones or only a single one of the friction wheels being drivable. The other friction wheels in this case would automatically co-rotate with the drive of a single friction wheel.

Figure 12:
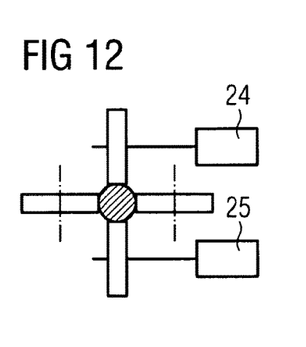

FIG. 12 shows an example of an implementation of a drive via two electric motors 24, 25.

Two friction wheels are represented in the FIGS. 4 to 6 schematically as cylindrical wheels, as the case may be with a friction coating.

Figure 13:
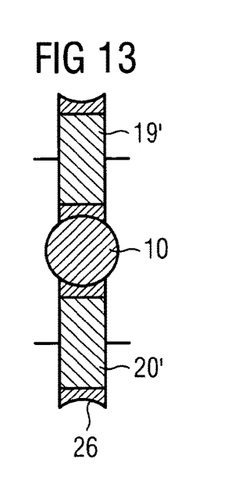

In contrast to this design, a concave outer peripheral surface of the friction wheel 19', 20' may also be provided according to FIG. 13. The concave surfaces 26 are designed in a manner such that they snugly bear on the elongate body 10 and also hold this laterally, so that one may ensure a reliable radial guiding of the elongate body already with two friction wheels.

Figure 14:
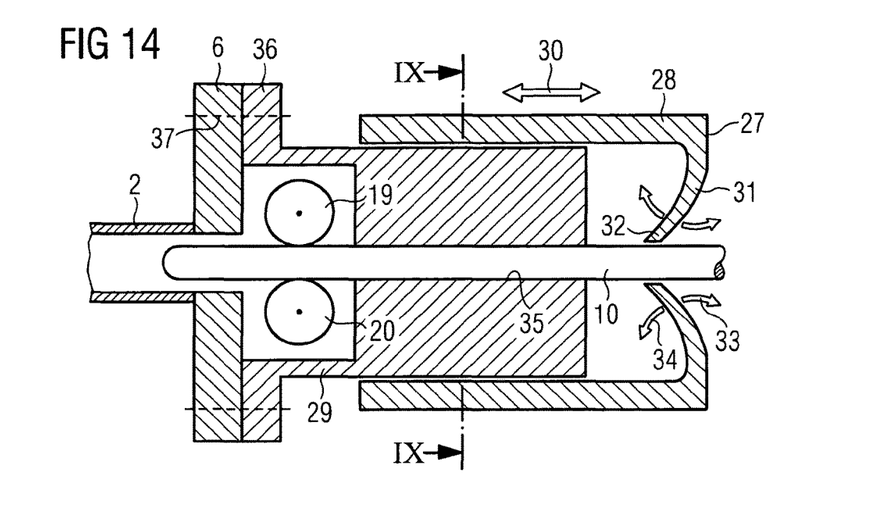

FIG. 14 shows an advance device with an axial force introduction unit 27 in the form of a push cylinder 28 which on a guide body 29 is displaceable to and fro in the direction of the arrow 30. The push cylinder 28 at one end comprises a bead-like disk 31 with a centric opening which is surrounded by a peripheral, movable lip 32. The opening is dimensioned in a manner such that the edge of the lip 32 lies on the elongate body 10. If the push cylinder 28 is pushed to the sheath 2, then the lip 32 is deflected in the direction of the arrow 33, and the centric opening of the bead disk 32 reduces in size and clamps the elongate body 10. This is then caught in the direction towards the sheath 2 and is displaced to there.

With a withdrawal movement of the push cylinder 28, the lip 32 moves in the direction of the arrow 34, so that the centric opening of the bead disk 31 is enlarged and the push cylinder 28 may be retracted with respect to the elongate body 10 which remains stationary.

In this manner, the elongate body 10 may be moved into the sheath 2 in steps. The movement of the push cylinder 28 is guided on the guide body 29, so that the movement path of the axial force introduction unit is fixed. The elongate body moreover is led in a cylindrical opening 35 of the guide body 29 and further in the direction of the sheath 2 through two or more friction wheels 19, 20 which are movable in a freely rotatable manner and lie opposite one another. A guiding by way of several groups of friction wheels, said groups lying axially behind one another, may be provided on the one hand, or exclusively by way of a long, hollow-cylindrical opening up to the flange 6 of the sheath 2.

Opposite the flange 6 of the sheath 2 lies a similarly constructed flange 36 of the guide body 29, so that the two flanges 6, 36 may be connected to one another by way of a screw connection which is shown by way of example by way of a dashed line 37. For this, several screws may be distributed on the periphery of the flange, in particular in a symmetrical manner.

Figure 15:
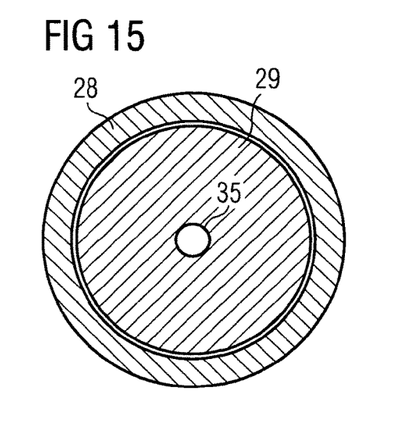

A cross section along the section line IX-IX in FIG. 14 is represented in FIG. 15, with the centric opening 15 in the guide body 29 which is surrounded by the cylinder 28 of the axial force introduction unit 27.

Figure 16:
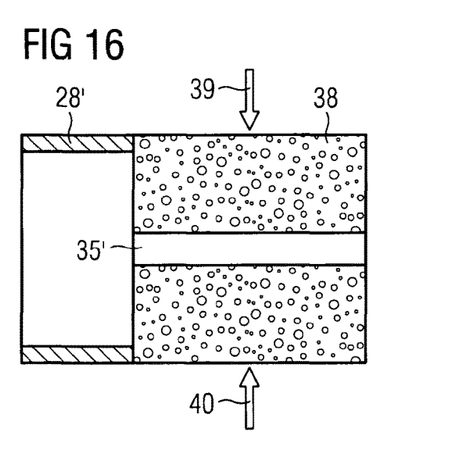

FIG. 16 shows another variant of an axial force introduction device which may be used for example in the push device according to FIG. 14 instead of the axial force introduction device 27. A push cylinder 28' is shown in FIG. 16, which may be guided in an axial manner on the guide body 29. A foam body 38 serves for clamping in the elongate body 10 and may be pressed together radially by way of pressure in the direction of the arrows 39, 40, in order to compress the opening 35' and to firmly clamp the elongate body in the opening 35'. For example, the foam cylinder 38 may be pressed together by hand, whilst simultaneously a push movement is carried out in the direction to the sheath 2. With this, the elongate body may be pushed somewhat into the sheath 2.

On retracting, the radial pressure on the foam cylinder 38 is reduced, so that the opening 35' elastically enlarges again in the radial direction and the elongate body is released. Thus the axial force introduction unit may then be retracted proximally with respect to the elongate body.

Figure 17:
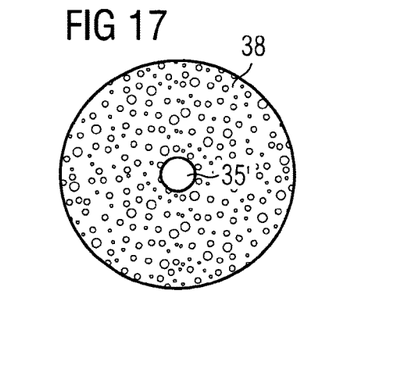

FIG. 17 shows a cross section through the foam cylinder 38 with the opening 35'.

Figure 18:
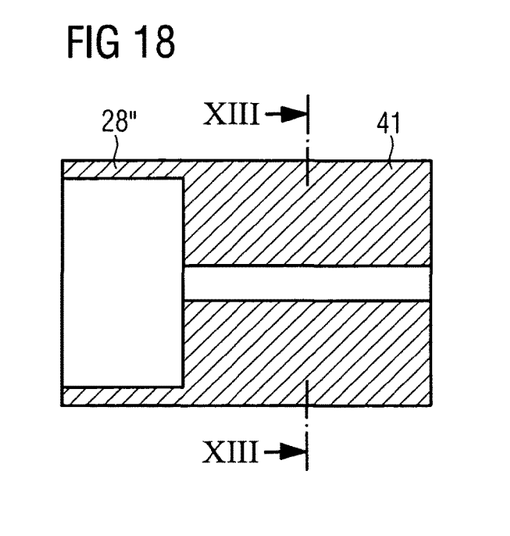

A further variant of an axial force introduction unit is represented in FIG. 18, with a solid push cylinder 41 which comprises a guide tube 28" which may be guided on the guide cylinder 29 as is represented in FIG. 14.

Figure 19:
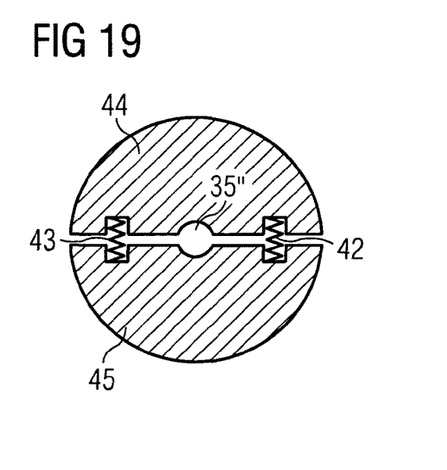
Figure 20:
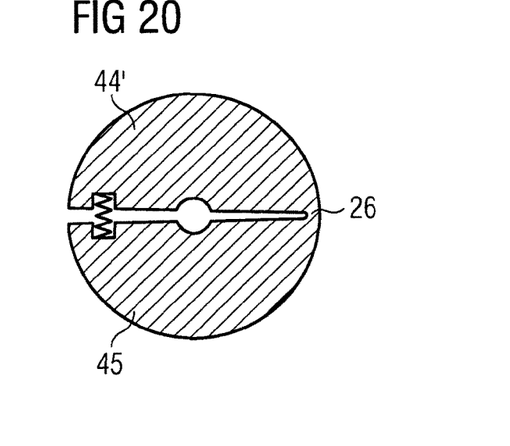

In the case which is represented in FIG. 18, the cylinder 41 itself is manufactured from an incompressible material, but is divided in the longitudinal direction into two halves, so that two segment bodies of the cylinder 41 result, as is represented in FIGS. 19 and 20 in different variants. Firstly, according to FIG. 19, the cylinder 41 may be completely cut through and consists of two halves 44, 45 connected only by springs 42, 43. These in the relaxed condition of the springs 42, 43 have a distance which is dimensioned such that the elongate body 10 is located in the central recess 35" with play. If the halves 44, 45 are pressed together against the force of the springs 42, 43, the elongate body may be clamped in the opening 35". The elongate body may then be advanced in the clamped condition. The two halves 44, 45 of the cylinder 41 may for example be pressed together by hand on manipulating the push device, and may be let go of when retracting the cylinder 41.

FIG. 20 shows a similar design form, wherein the cylinder 41 is not completely separated into two halves, but a film joint 46 remains on one side of the cylinder 41, and this joint permits the two halves 44', 45' to be folded open. One may also provide a separate hinge instead of the film joint 26. The manner of functioning on clamping the elongate body corresponds to that represented by way of FIG. 19.

Figures 21, 22:
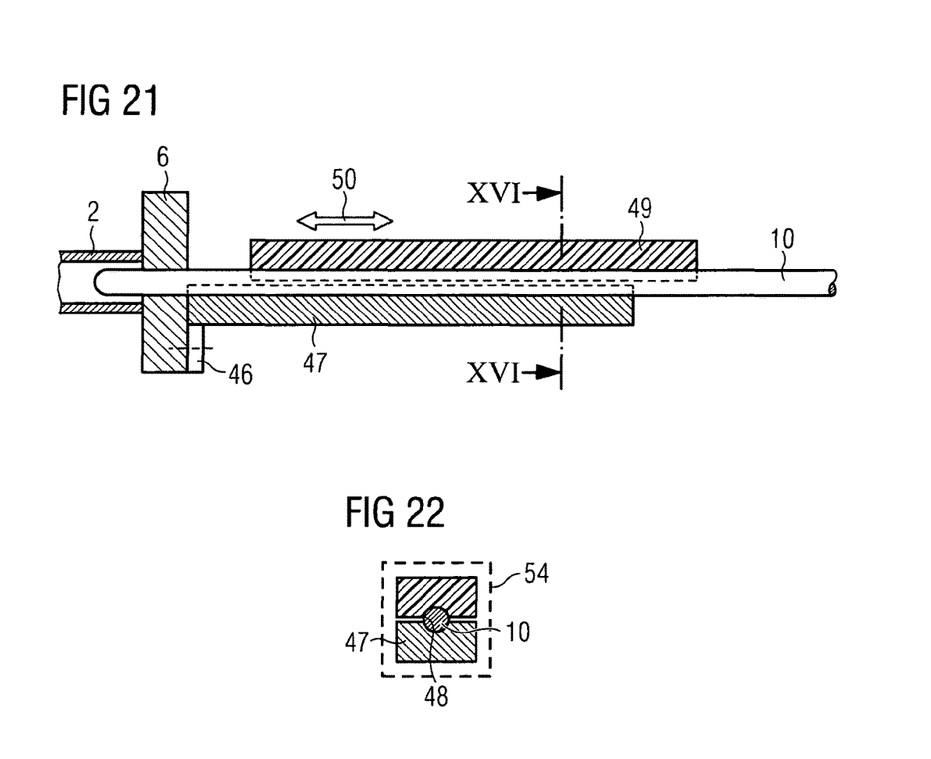

FIG. 21 shows a push device which is different from the devices which are represented in the previous figures. Here, a flange 46 of a guide body 47 is fastened on a sheath 2, and to be more specific, on its flange 6. The guide body 47 comprises a guide rail for the elongate body 10 which for example may be given by a semi-cylindrical or part-cylindrical recess, in which the elongate body 10 may lie.

FIG. 22 in a cross section shows the guide body 47 with the part-cylindrical recess 48 in which the elongate body 10 lies.

In FIG. 21, a drive body 49 is represented above the guide body 47, and this drive body forms the axial force introduction unit. This drive body 49 for example likewise comprise a part-cylindrical recess which receives the elongate body 10 at least partly. The drive body 49 may be displaced proximally or distally in the axial direction, represented by the double arrow 50. A particular feature of the guide body 47 and of the drive body 49 may for example be realised by way of the friction between the drive body 49 and the elongate body 10 on account of the material selection with higher coefficients of static friction, being significantly larger than the friction between the elongate body 10 and the guide body 47. For example, the guide body 47 may consist of a particularly smooth material with a low coefficient of friction, for example PTFE or may be coated with such a material.

The drive body 49 for its part may consist of a material which has a greater coefficient of friction compared to the elongate body 10, such as of an elastomer, particularly rubber or silicone rubber. By way of this, if the drive body 49 is pressed radially against the elongate body 10, the elongate body 10 may be moved axially in the fixed guide rail by way of displacement of the drive body in the axial direction.

Usefully, on introducing the elongate body 10 into the sheath 2, this is simultaneously pressed onto the drive body and moves this distally in the direction of the sheath 2. On retracting the drive body away from the sheath 2, the pressing force on the elongate body is reduced, so that this is not caught and remains in the sheath 2. In this manner, the elongate body may be moved along in the sheath 2 in steps.

Figure 23:
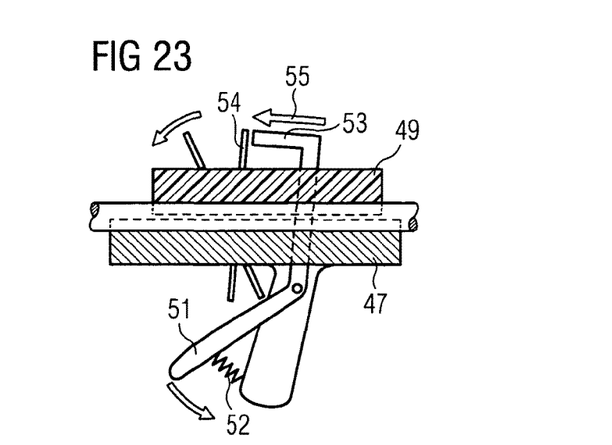

According to FIG. 23, a pistol-like handgrip may also be provided on the guide body 47 and this hand grip comprises a lever 51 which is movable against a spring 52. The lever 51 is pivotably mounted and comprises a plunger 53 which presses against a clamping disk 54, clamps this with respect to the drive body 49 and thereupon effects a push movement of the drive body 49. The clamping disk is spring-loaded opposite to the direction of the arrow 55.

The device shown in the FIGS. 9-23 may on the one hand be used for a second sheath, in order to press this as an elongate body against a first sheath and to permit the pushing-through of a pump head with a minimised risk of a buckling of the pump catheter. On the other hand, this device may also be connected proximally to a holding device of a second sheath which is shown in the FIGS. 3-8, in order to permit the inserting of a catheter (as the case maybe with a pump head) into the second sheath without a buckling. Thus two push devices may be combined with one another in this manner.

The invention claimed is:

1. A push device system for the axial insertion of a blood pump into a sheath, the push device system comprising:
    a compressible and self-expandable pump head configured to expand in a heart chamber, and
    a drive shaft coupled to a proximal region of the blood pump;
    a sheath having proximal-most and distal-most ends and an axis, with an inner lumen configured to receive the pump head and the drive shaft through the proximal-most end of the sheath,
    a holding element having proximal and distal regions, a flange at the distal region of the holding element, a distal-most end of the flange comprising a distal surface that abuts a proximal surface of the proximal-most end of the sheath to couple the holding element directly to the proximal-most end of the sheath, wherein the holding element is non-positively coupled to the blood pump; and
    wherein the holding element is configured to apply an axial holding force or a push force onto the blood pump and is arranged to remain stationary relative to the sheath.

2. The push device system according to claim 1, wherein the holding element is connected to the sheath by a central thread, a bayonet closure, by way of a fit surface by way of adhesion forces, by way of a magnetic device, by way of an eccentric screw connection, by way of a gluing connection, a cone connection, a snap connection, an electrostatic connection, by way of elastic holding elements or by way of inserting a fit piece of the sheath into a fittingly shaped recess of the holding element.

3. The push device system of claim 1, wherein the drive shaft is contained within a catheter.

4. The push device system of claim 1, wherein the holding element is configured to apply the push force on the catheter.

5. The push device system of claim 1, wherein the pump head is configured to be compressed within the holding element and within the sheath.

6. The push device system of claim 1, wherein the holding element is configured to couple to the drive shaft and apply the push force on the drive shaft.

7. The push device system of claim 1, wherein the holding element is configured to limit radial deflections of the sheath by minimizing a distance between (i) where the axial holding force or push force is applied onto the blood pump and (ii) the proximal-most end of the sheath.

8. The push device system according to claim 1, wherein a speed of advance of the blood pump is controlled.

9. The push device system according to claim 8, wherein the push force and a push movement is controlled in dependence on a push resistance of the blood pump.

10. The push device system according to claim 1, wherein the blood pump is configured to rotate about a longitudinal axis.

11. The push device system of claim 10, wherein the blood pump is configured to rotate at a high rotation speed to deliver blood out of a heart and into a blood vessel.

12. The push device system of claim 1, wherein the proximal surface of the proximal-most end of the sheath is oriented at a first non-zero angle relative to the axis of the sheath, and the distal surface of the distal-most end of the flange is oriented at a second non-zero angle relative to the axis of the sheath.

13. The push device system of claim 12, wherein the first non-zero angle and the second non-zero angle are both about 90 degrees.

14. The push device system according to claim 1, wherein a guide device is coupled to the sheath and the guide device is configured to radially support the blood pump, wherein the holding element is either arranged in a stationary manner relative to the guide device or is guided on a predefined movement path.

15. The push device system according to claim 14, wherein the holding element comprises a radial clamping device which by way of pressing a clamping tool onto the blood pump in the radial direction, produces an adhesion to the blood pump, which serves for applying a push force or holding force in the axial direction of the blood pump.

16. The push device system according to claim 15, wherein the clamping tool is configured to roll on the blood pump.

17. The push device system according to claim 16, wherein the clamping tool comprises at least two friction wheels, and the at least two friction wheels at least partly lie opposite one another with respect to the blood pump.

18. The push device system according to claim 17, wherein the at least two friction wheels are controllable with regard to their rotation.

* * * * *

UNITED STATES PATENT AND TRADEMARK OFFICE
CERTIFICATE OF CORRECTION

PATENT NO. : 10,391,278 B2
APPLICATION NO. : 13/261735
DATED : August 27, 2019
INVENTOR(S) : Schulz et al.

Page 1 of 1

It is certified that error appears in the above-identified patent and that said Letters Patent is hereby corrected as shown below:

In the Specification

Column 1, Line 51, after "lumen", insert --.--

Column 8, Line 57, delete "19, 20" and insert --22, 23--

Column 9, Line 38, delete "32" and insert --31--

Signed and Sealed this
Seventh Day of December, 2021

Drew Hirshfeld
*Performing the Functions and Duties of the
Under Secretary of Commerce for Intellectual Property and
Director of the United States Patent and Trademark Office*